US012458724B1

(12) United States Patent
Habbel

(10) Patent No.: US 12,458,724 B1
(45) Date of Patent: Nov. 4, 2025

(54) SCENT DISPENSING SYSTEMS AND RELATED METHODS

(71) Applicant: Arizona Air-Scent, Inc., Scottsdale, AZ (US)

(72) Inventor: Sam Habbel, Scottsdale, AZ (US)

(73) Assignee: Arizona Air-Scent, Inc., Scottsdale, AZ (US)

( * ) Notice: Subject to any disclaimer, the term of this patent is extended or adjusted under 35 U.S.C. 154(b) by 490 days.

(21) Appl. No.: 18/193,323

(22) Filed: Mar. 30, 2023

Related U.S. Application Data

(60) Provisional application No. 63/362,193, filed on Mar. 30, 2022.

(51) Int. Cl.
*A61L 9/14* (2006.01)

(52) U.S. Cl.
CPC .................................... *A61L 9/14* (2013.01)

(58) Field of Classification Search
CPC ........................................................ A61L 9/14
See application file for complete search history.

(56) References Cited

U.S. PATENT DOCUMENTS

| | | | | |
|---|---|---|---|---|
| 9,296,549 B2 | 3/2016 | Ghavami-Nasr et al. | | |
| 10,071,849 B2 | 9/2018 | Nasr et al. | | |
| 2006/0226251 A1* | 10/2006 | Helf | A61L 9/037 239/34 | |
| 2013/0126639 A1 | 5/2013 | Tu | | |
| 2022/0323631 A1* | 10/2022 | Sward | B60H 3/0007 | |

FOREIGN PATENT DOCUMENTS

| | | | |
|---|---|---|---|
| CN | 203598271 U | 5/2014 | |
| CN | 206145881 U | 5/2017 | |
| CN | 107744909 A | 3/2018 | |
| CN | 209628643 U | 11/2019 | |
| CN | 211157534 U | 8/2020 | |
| CN | 216394853 U | 4/2022 | |
| CN | 216417896 U | 5/2022 | |
| WO | WO-2020019028 A1 * | 1/2020 | A61L 2/22 |

* cited by examiner

*Primary Examiner* — Timothy C Cleveland
(74) *Attorney, Agent, or Firm* — IPTechLaw

(57) ABSTRACT

Implementations of a scent dispenser may include a front panel and a rear panel, the front panel having a side surface extending around edges of the front panel and the rear panel having a side surface extending around edges of the rear panel, the side surface of the front panel and the side surface of the rear panel configured to align to form an enclosure therein. The dispenser may include a first dispensing opening in the front panel; a second dispensing opening formed partly in the side surface of the front panel and partly in the side surface of the rear panel; a diffuser supported in the enclosure, the diffuser including a first dispensing orifice extending toward the first dispensing opening and a second dispensing orifice extending toward the second dispensing opening; and a plug configured to be inserted into either the first dispensing orifice or the second dispensing orifice.

20 Claims, 6 Drawing Sheets

SCENT DISPENSING SYSTEMS AND RELATED METHODS

CROSS REFERENCE TO RELATED APPLICATIONS

This document claims the benefit of the filing date of U.S. Provisional Patent Application 63/362,193, entitled "Scent Diffuser Systems and Related Methods" to Sam Habbel which was filed on Mar. 30, 2022, the disclosure of which is hereby incorporated entirely herein by reference.

BACKGROUND

1. Technical Field

Aspects of this document relate generally to systems for dispensing fine mists and/or atomized particles. Particular implementations also include systems for dispensing scents via the fine mists/atomized particles.

2. Background

Scent dispensing systems have been devised to allow for release of fragrances into an area like a room. The fragrance can be designed to create a desired impression or memory or to help conceal an odor present in the room.

SUMMARY

Implementations of a scent dispenser may include a front panel and a rear panel, the front panel having a side surface extending around edges of the front panel and the rear panel having a side surface extending around edges of the rear panel, the side surface of the front panel and the side surface of the rear panel configured to align to form an enclosure therein. The dispenser may include a first dispensing opening in the front panel; a second dispensing opening formed partly in the side surface of the front panel and partly in the side surface of the rear panel; a diffuser supported in the enclosure, the diffuser including a first dispensing orifice extending toward the first dispensing opening and a second dispensing orifice extending toward the second dispensing opening; and a plug configured to be inserted into either the first dispensing orifice or the second dispensing orifice.

Implementations of scent dispensers may include one, all, or any of the following:

The front panel and the rear panel may be coupled together through magnetic fasteners.

The rear panel may include a mounting structure configured to mount the scent dispenser to a support surface.

An alignment of the first dispensing opening from the second dispensing opening may be substantially 90 degrees.

The diffuser may include a mounting projection configured to be received into a mounting port of the rear panel.

The mounting projection may include an electrically conductive portion that electrically couples the diffuser with an electrical control system.

The rear panel may include at least one air intake opening therein in fluid connection with an air intake of the diffuser.

Implementations of a scent dispenser may include a front panel and a rear panel, the front panel having a side surface extending around edges of the front panel and the rear panel having a side surface extending around edges of the rear panel, the side surface of the front panel and the side surface of the rear panel configured to align to form an enclosure therein; and a first dispensing opening and a third dispensing opening in the front panel. The scent dispenser may further include a second dispensing opening and a fourth dispensing opening formed partly in the side surface of the front panel and partly in the side surface of the rear panel; a first diffuser supported in the enclosure, the first diffuser including a first dispensing orifice extending toward the first dispensing opening and a second dispensing orifice extending toward the second dispensing opening; and a second diffuser supported in the enclosure, the second diffuser including a third dispensing orifice extending toward the third dispensing opening and a fourth dispensing orifice extending toward the fourth dispensing opening. The scent dispenser may include a first plug configured to be inserted into either the first dispensing orifice or the second dispensing orifice and a second plug configured to be inserted into either the third dispensing orifice or the fourth dispensing orifice.

Implementations of a scent dispenser may include one, all, or any of the following:

The front panel and the rear panel may be coupled together through magnetic fasteners.

The rear panel may include a mounting structure configured to mount the scent dispenser to a support surface.

An alignment of the first dispensing opening from the second dispensing opening may be substantially 90 degrees and an alignment of the third dispensing opening from the fourth dispensing opening may be substantially 90 degrees.

The first diffuser may include a first mounting projection configured to be received into a first mounting port of the rear panel and the second diffuser may include a second mounting projection configured to be received into a second mounting portion of the rear panel.

The first mounting projection and the second mounting projection may each include an electrically conductive portion that electrically couples the first diffuser and the second diffuser, respectively, with an electrical control system.

The rear panel may include at least one air intake opening therein in fluid connection with an air intake of the first diffuser and with an air intake of the second diffuser.

Implementations of a scent dispenser may include a front cover and a rear cover surrounding an enclosure therein, the front cover and rear cover including a side surface between the front cover and the rear cover; a first dispensing opening in the front panel; and a second dispensing opening formed in the side surface. The scent dispense may include a diffuser supported in the enclosure, the diffuser including a first dispensing orifice extending toward the first dispensing opening and a second dispensing orifice extending toward the second dispensing opening; and a plug configured to be inserted into either the first dispensing orifice or the second dispensing orifice.

Implementations of scent dispensers may include one, all, or any of the following:

The front cover and the rear cover may be coupled together through magnetic fasteners.

An alignment of the first dispensing opening from the second dispensing opening may be substantially 90 degrees.

The diffuser may include a mounting projection configured to be received into a mounting port of the rear cover.

The mounting projection may include an electrically conductive portion that electrically couples the diffuser with an electrical control system.

The rear cover may include at least one air intake opening therein in fluid connection with an air intake of the diffuser.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

This disclosure, its aspects and implementations, are not limited to the specific components, assembly procedures or method elements disclosed herein. Many additional components, assembly procedures and/or method elements known in the art consistent with the intended scent dispensing systems will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such scent dispensing systems, and implementing components and methods, consistent with the intended operation and methods.

Examples of atomizing devices/diffuser systems that may be utilized in various scent dispensing systems like those disclosed herein may be found in the Chinese Utility Model application No. 202121875207.5 to Gao and Habbel, filed Aug. 11, 2021, entitled "Atomizing Container and Atomizing Apparatus;" in the Chinese Utility Model application Ser. No. 20/212,1875154.7 to Gao and Habbel, filed Aug. 11, 2021, entitled "Atomizing Apparatus;" the Patent Cooperation Treaty Application App. No. PCT/CN2022/111495 to Gao and Habbel entitled "Atomizing Container and Atomizing Apparatus," filed Aug. 10, 2022; and in the U.S. patent application application Ser. No. 18/247,327 to Gao and Habbel entitled "Atomizing Container and Atomizing Apparatus," filed Mar. 30, 2023; the disclosures of each of which are hereby incorporated entirely herein by reference.

One of the challenges for scent dispensing systems is that particular use situations and, at times, user preferences, lead to the need to direct a stream of scent in a vertical direction relative to the mounted/placed location of the system or in a horizontal direction. Various scent dispensing systems have been devised that direct the stream of scent in only one direction at a time, and that direction cannot be changed post-manufacture by the user. Thus, the user may find themselves with a scent dispensing system that is not able to send the stream of scent in the needed direction when mounted/located in the place available for use. Implementations of scent dispensing systems that can be user configured to dispense a stream of scent in either a vertical or horizontal direction or substantially vertical or substantially horizontal direction are disclosed in this document. Single stream scent dispensing systems and multiple stream scent dispensing systems are also disclosed in this document.

Figure 1:
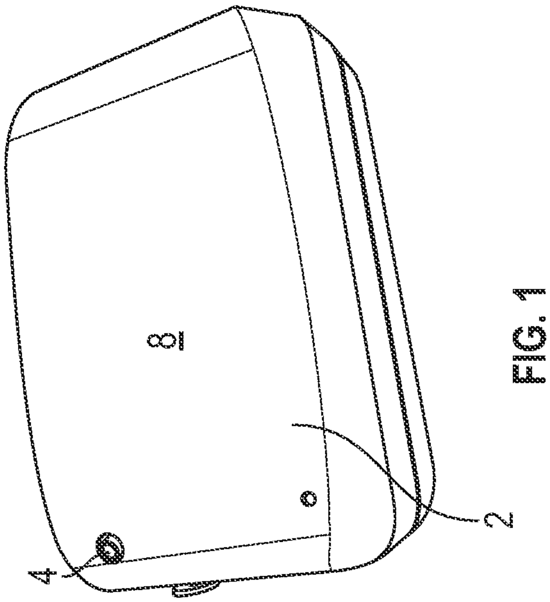
FIG. 1 is a perspective view of a front panel/cover of an implementation of a scent dispenser in a horizontal orientation.
Figure 2:
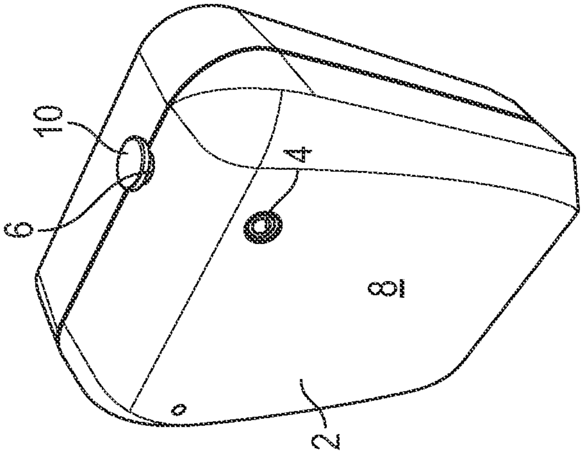
FIG. 2 is a perspective view of the implementation of the scent dispenser of FIG. 1 in a vertical orientation.
Figure 3:
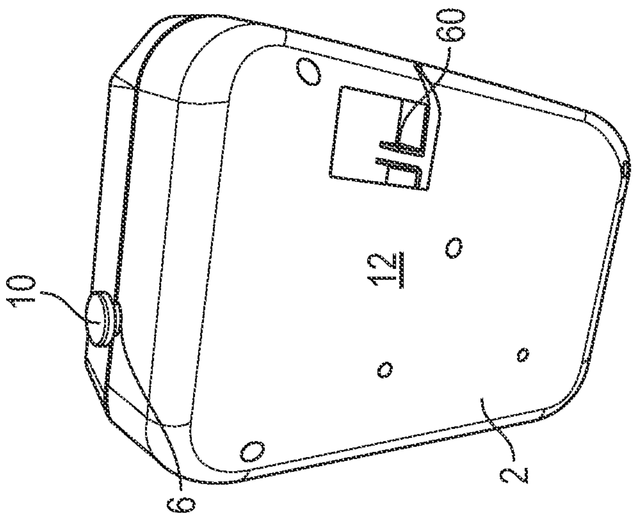
FIG. 3 is a perspective view of a rear cover/panel of the implementation of the scent dispenser of FIG. 1.

Referring to FIGS. 1-3, an implementation of a single stream scent dispenser 2 is illustrated showing the unit in front, perspective, and rear views, respectively. As illustrated, the scent dispenser 2 includes a first dispensing opening 4 that extend through a first dispensing opening in a front cover/panel 8 of the dispenser 2. The scent dispenser 2 also includes a second dispensing opening 6 formed in a part of the front cover/panel 8 and a part of the rear cover panel 12. A plug 10 is illustrated inserted into a second dispensing orifice 6 of a diffuser/atomizer (not visible in FIGS. 1-3) included inside the enclosure formed between the front cover and rear cover which serves to prevent flow of scent out of the second orifice from the diffuser included within the dispenser 2. In the implementation illustrated in FIGS. 1-3, the plug 10 fits into the second orifice 6 (or the first orifice 4) via a friction fit and can be removed and inserted by the user either prior to or after installation of the dispenser 2 via mounting or placement at a desired location. Other methods of fastening the plug to the orifice could also be used, including, by non-limiting example, screwing, retaining via clips, rotating, or any other structure of method of removably retaining an object into a tube. Rear cover/panel 12 of the diffuser 2 is designed with one or more mounting features 60 to allow the unit to be mounted/placed as desired on a support surface, such as, by non-limiting example, a wall, ceiling, half wall, counter, cabinet, or other structural surface.

Figure 4:
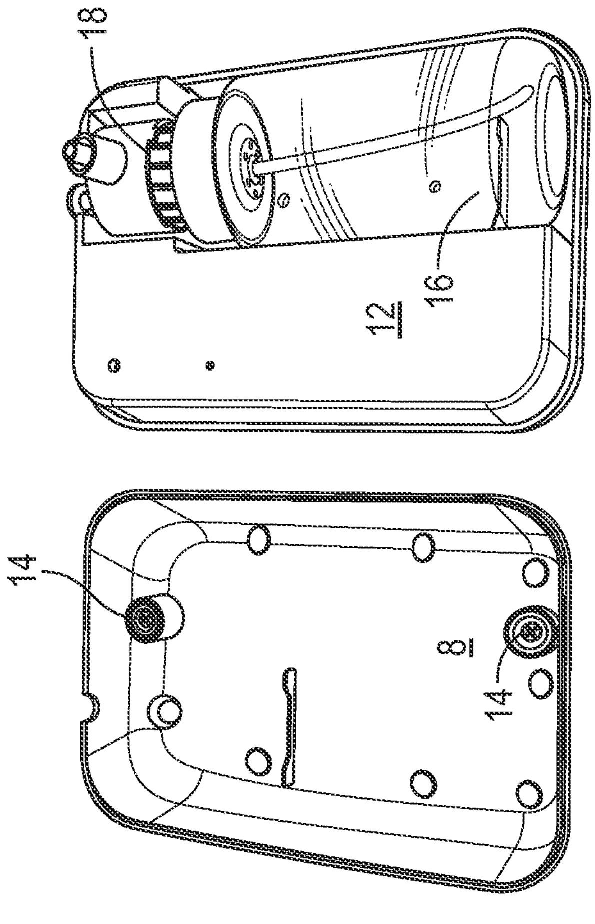
FIG. 4 is a perspective view of the implementation of the scent dispenser of FIG. 1 with the front panel separated from the rear panel showing a diffuser.

Referring to FIG. 4, the dispenser 2 is illustrated with the front cover/panel 8 separated from the rear cover/panel through disengaging magnetic fasteners 14. As illustrated, the fastener portions 14 on the front cover 8 engage magnetically (attractively) with corresponding magnetic fasteners behind the material of the rear cover 12. In various implementations, the magnetic fasteners 14 of the front cover 8 may be magnetizable, or made of a magnetizable material like a ferrous metal and the magnetic fasteners of the rear cover 12 may be magnets. In other implementations, the reverse may be true including where one of the front cover fasteners is a magnet while the other is made of a magnetizable material. The ability to use magnetic fasteners may significantly ease the process of removing and replacing the cover to replace the scent reservoir 16 coupled with the diffuser/atomizer 18 illustrated in FIG. 4.

Figure 5:
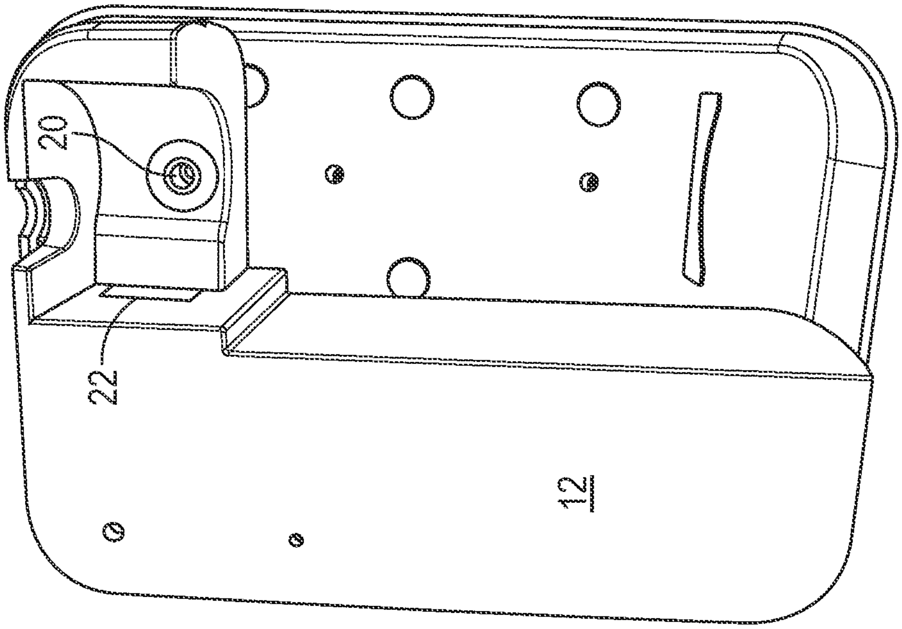
FIG. 5 is a top view of a rear panel of the implementation of the scent dispenser of FIG. 1.

FIG. 5 illustrates rear cover 12 with the diffuser/atomizer and scent reservoir removed showing mounting port 20 which mechanically holds the atomizer in place and also electrically couples the electrical components of the atomizer to the power supply and electrical control system included within the rear panel of the dispenser 2. Air flow opening 22 is also included in the structure of the rear cover 12 to allow air to be drawn into the atomizer through a corresponding opening that will be described hereafter. The air flow opening 22 is in fluid connection with an air intake opening of the rear panel to allow air to flow into the diffuser.

Figure 7:
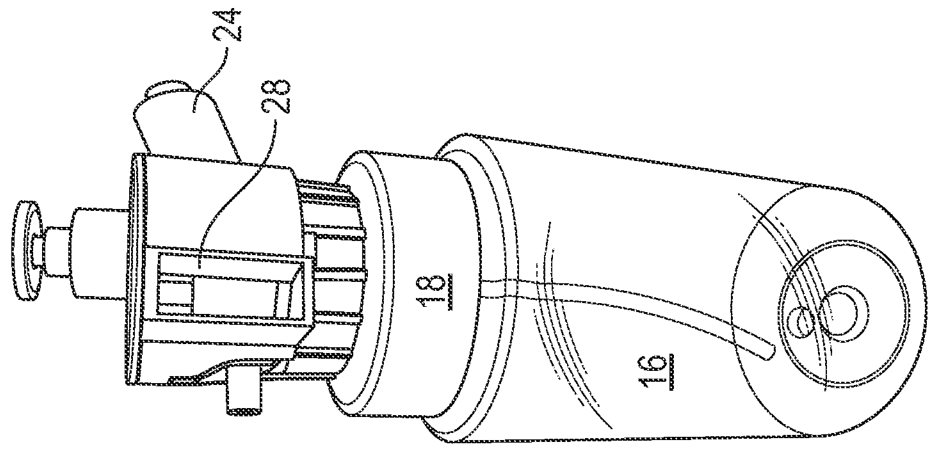
FIG. 7 is a side view of the diffuser implementation of FIG. 6.
Figure 6:
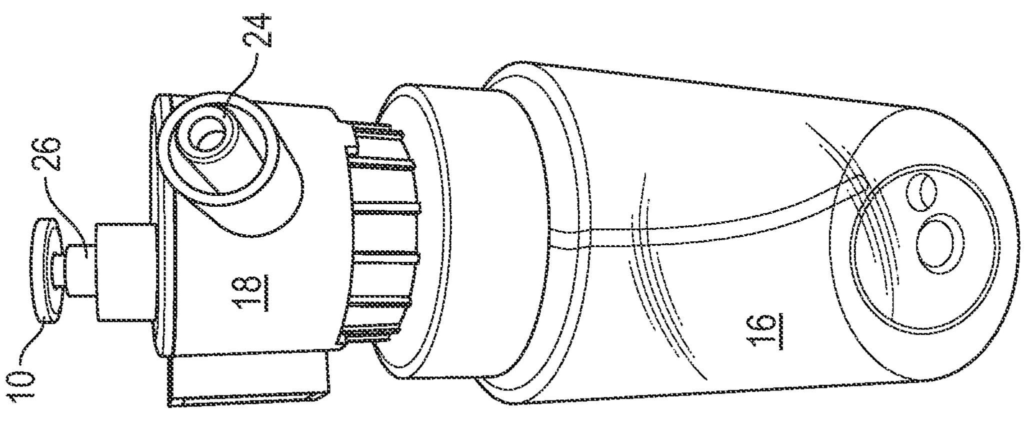
FIG. 6 is a front view of an implementation of a diffuser.

Referring to FIGS. 6-9, various front, side, rear, and top views of an implementation of a diffuser/atomizer 18 coupled with a scent reservoir 16 are illustrated. FIG. 6 illustrates front dispensing tube/first dispensing orifice 24 and top dispensing tube/second dispensing orifice 26 which has plug 10 inserted therein. FIG. 7 illustrates how the front dispensing tube 24, in some implementations, may be angled toward the vertical where it meets the body of atomizer 18 to assist with lofting the stream of scent when the scent is being dispensed substantially horizontally. FIG. 7 also illustrates air intake opening 28 of the atomizer 18 that receives air from the air flow opening 22 of the rear cover 12. During operation, a fan within the atomizer (not shown in FIG. 7) works to draw ambient air into the body of the atomizer through the air intake opening 28 and then the air containing the atomized scent/fragrance is dispensed out through either the front dispensing tube 24 or the top dispensing tube 26, depending on which is plugged by the user using plug 10. In some implementations, the plug may be omitted and scent dispensed in both the horizontal and vertical directions using both tubes, but in such implementations, because the volume of scent is now divided between the two tubes, the directionality of the scent dispensing may be substantially reduced. The use of the plug assists with ensuring that the stream of scent moves in either the vertical or horizontal directions as desired. The ability to directionally send the scent may allow the user to ensure the fragrance arrives where desired consistently. As illustrated in FIGS. 6-9, an angle between the first dispensing orifice 14 and the second dispensing orifice 26 is substantially 90 degrees, depending on how much additional lofting angle is applied to the tube from which first dispensing orifice 24 opens.

Figure 9:
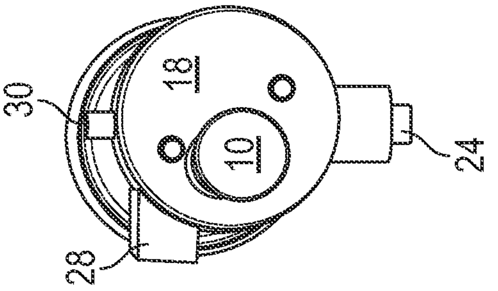
FIG. 9 is a top view of the diffuser implementation of FIG. 6.
Figure 8:
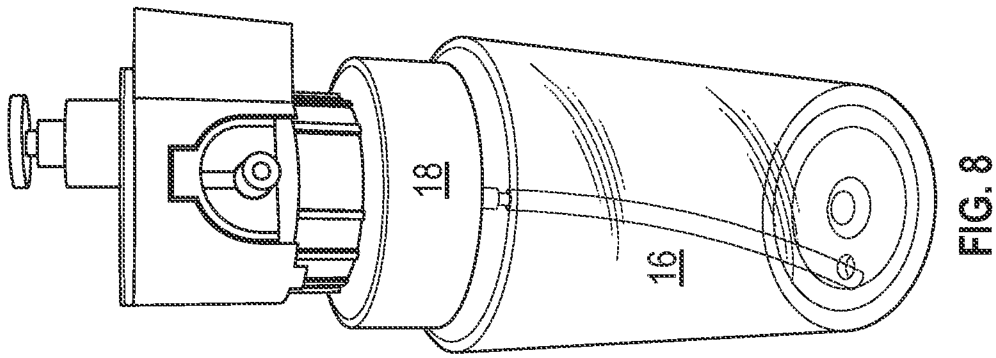
FIG. 8 is a rear view of the diffuser implementation of FIG. 6.
Figure 15:
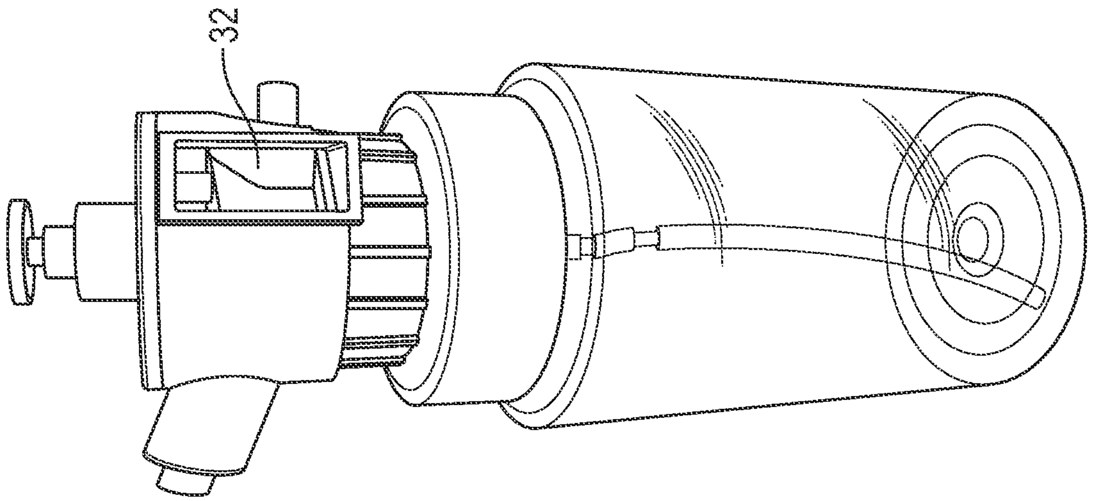
FIG. 15 is a side view of a diffuser showing an air intake.

FIG. 8 is a rear view of the atomizer 18 and shows mounting projection 30 that is designed to friction fit into mounting port 20 of the rear cover 12. In various implementations, an electrical contact may be inserted into the center of the mounting projection 30 from the mounting port 20 and in others, the interior/exterior of the mounting projection 30 may be electrically conductive to allow for electrical connections to be made to power the fan and other electrical components within the atomizer. FIG. 9 is a top view of the atomizer 18 and shows the relative relationships of the mounting projection 30, front dispensing tube 24, plug 10, and air intake opening 28 of the atomizer 18. In various implementations, and as illustrated in FIG. 15, the atomizer 18 can have a left handed arrangement as in FIG. 9 or may be right handed as in FIG. 15 depending on which side of the atomizer the air intake opening 28, 32 is aligned with.

Figure 11:
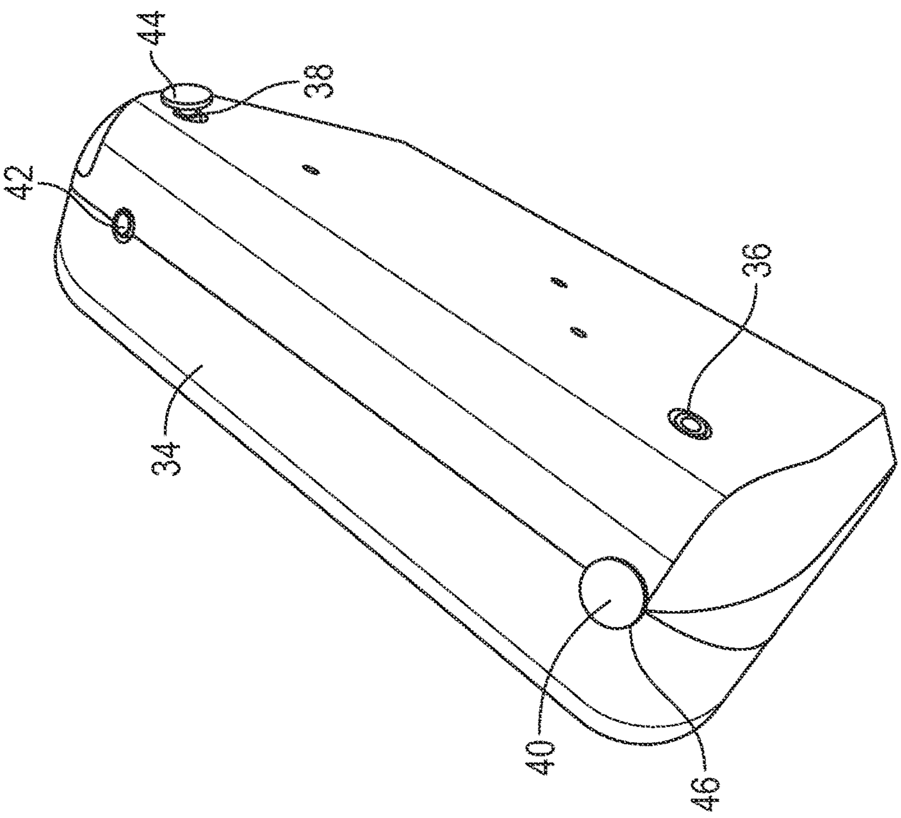
FIG. 11 is a perspective view of the scent dispenser of FIG. 10 showing a rear panel.
Figure 10:
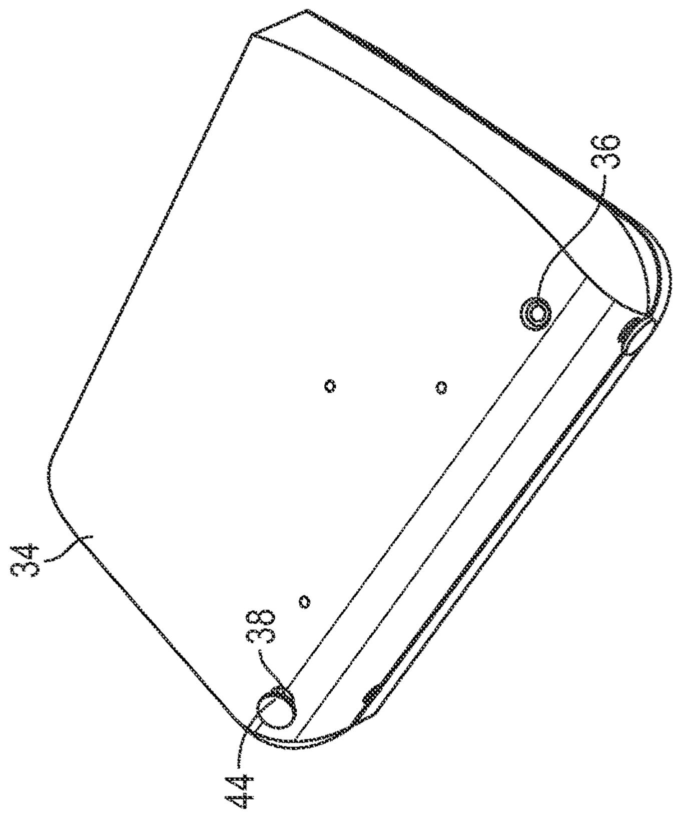
FIG. 10 is a front view of an implementation of a scent dispenser showing a front panel.

The ability to have right and left handed atomizers may enable the use of multiple atomizers in the same dispenser case as in the dispenser implementation 34 illustrated in FIGS. 10-11. FIG. 10 illustrates a front view, and FIG. 11 illustrates a perspective view showing front dispensing openings/first and third dispensing openings 36, 38 and top dispensing openings/second and fourth dispensing openings 40, 42. Plugs 44, 46 are inserted into front dispensing orifice 38 and top dispensing orifice 40, respectively. In this configuration, as there are two atomizers/diffusers included within the dispenser 34, one atomizer will emit a stream of scent vertically through top dispensing orifice 42 while the other atomizer will emit a stream of scent horizontally through front dispensing orifice 36. In other implementations, however, the user may plug both of the top dispensing orifices/second and fourth dispensing orifices 40, 42 or both of the front dispensing orifices/first and third dispensing orifices 36, 38 to direct both streams of scent horizontally or vertically, respectively. Any of a wide variety of configurations are possible as is a configuration where one or both of the atomizers has both dispensing tubes open. However, in such a configuration, as previously discussed, the scent dispensed will be of low directionality.

Furthermore, in some dispenser implementations, more than two sets of dispensing openings may be employed to accommodate a corresponding three or more diffusers using the principles disclosed in this document. In such implementations, as in the two diffuser implementations, a different fragrance may be included in each of the diffusers, and the combination of the two fragrances may create the desired overall scent.

Figure 13:
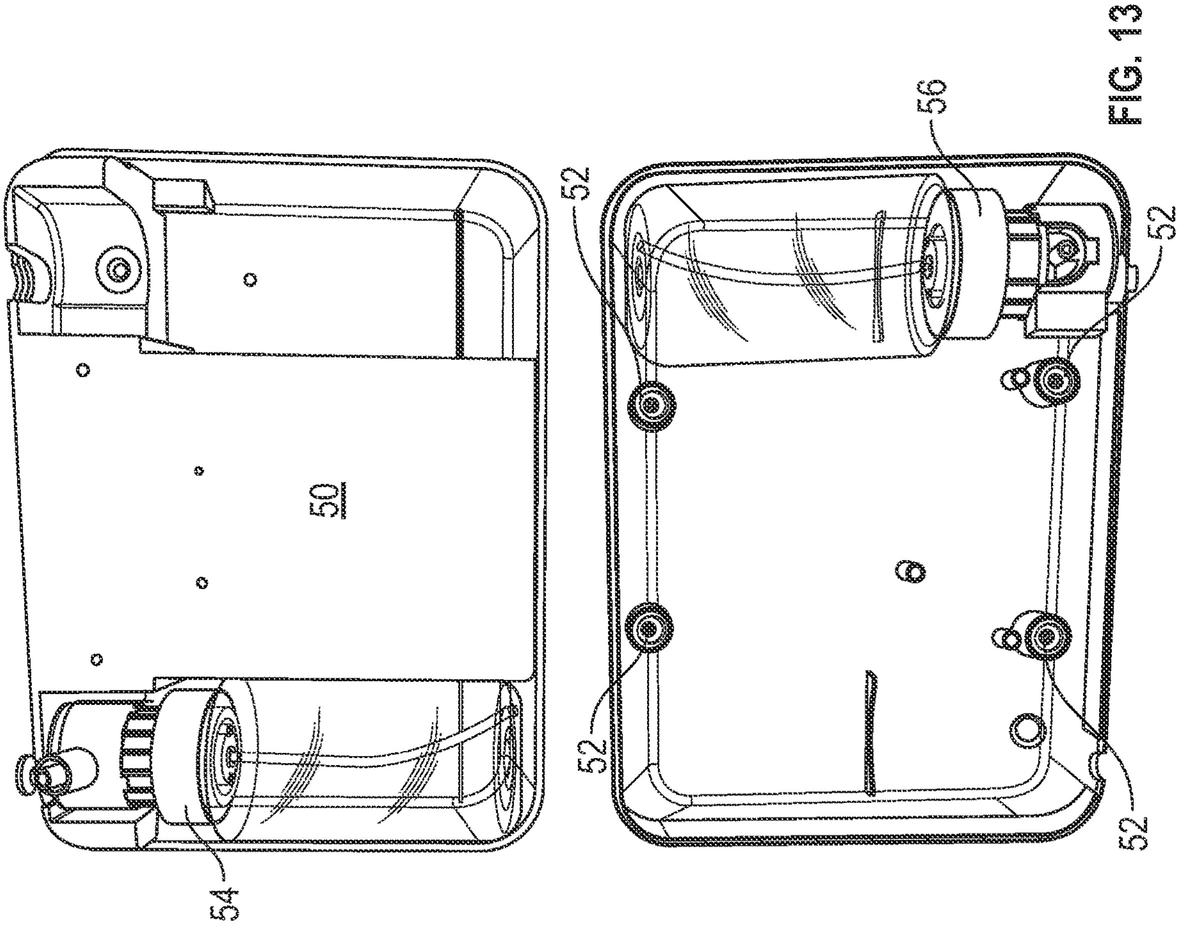
FIG. 13 is a top view of the front panel and rear panel of the scent dispenser of FIG. 10 each with a diffuser coupled therein.
Figure 12:
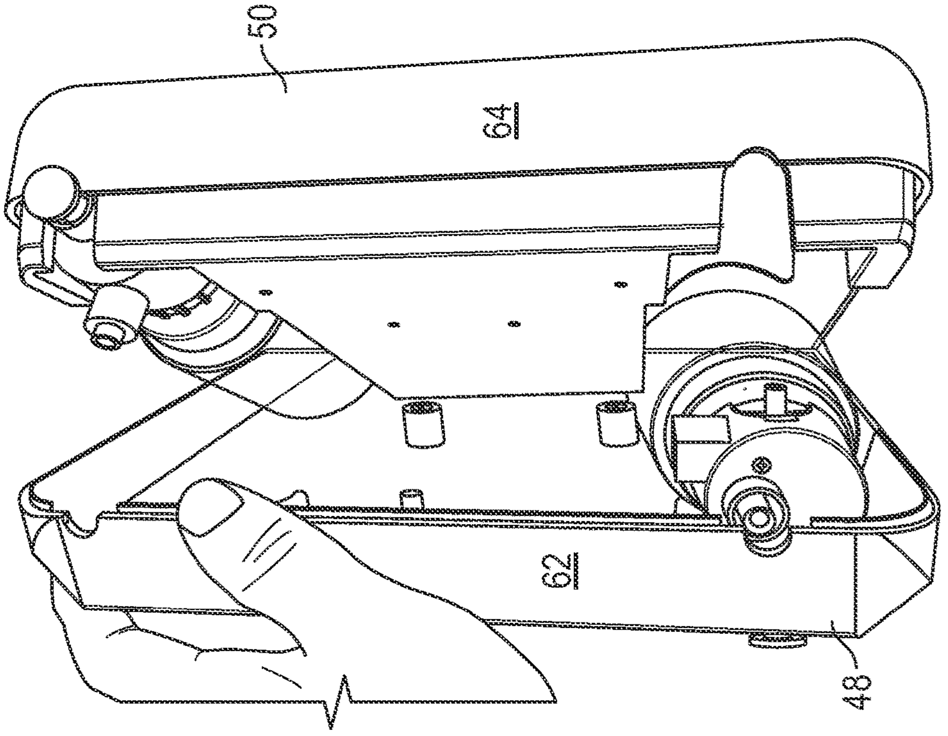
FIG. 12 is a partially opened view of the front panel and rear panel of the scent dispenser of FIG. 10 showing two diffusers therein.

Referring to FIG. 12, the dispenser 34 is illustrated with the front cover/panel 48 partially separated from the rear cover/panel 50 with FIG. 13 showing both covers fully separated from each other. In this view, like the dispenser 2 implementation of FIGS. 1-3, the side surface 62 of the front panel and the side surface 64 of the rear panel each form a surface that extends around the edges of each of the front panel and the rear panel, respectively. The two side surfaces 62, 64 collectively form a side surface of the dispenser 34 that allows the front panel 48 and rear panel 50 to form an enclosure between the front cover.

Figure 14:
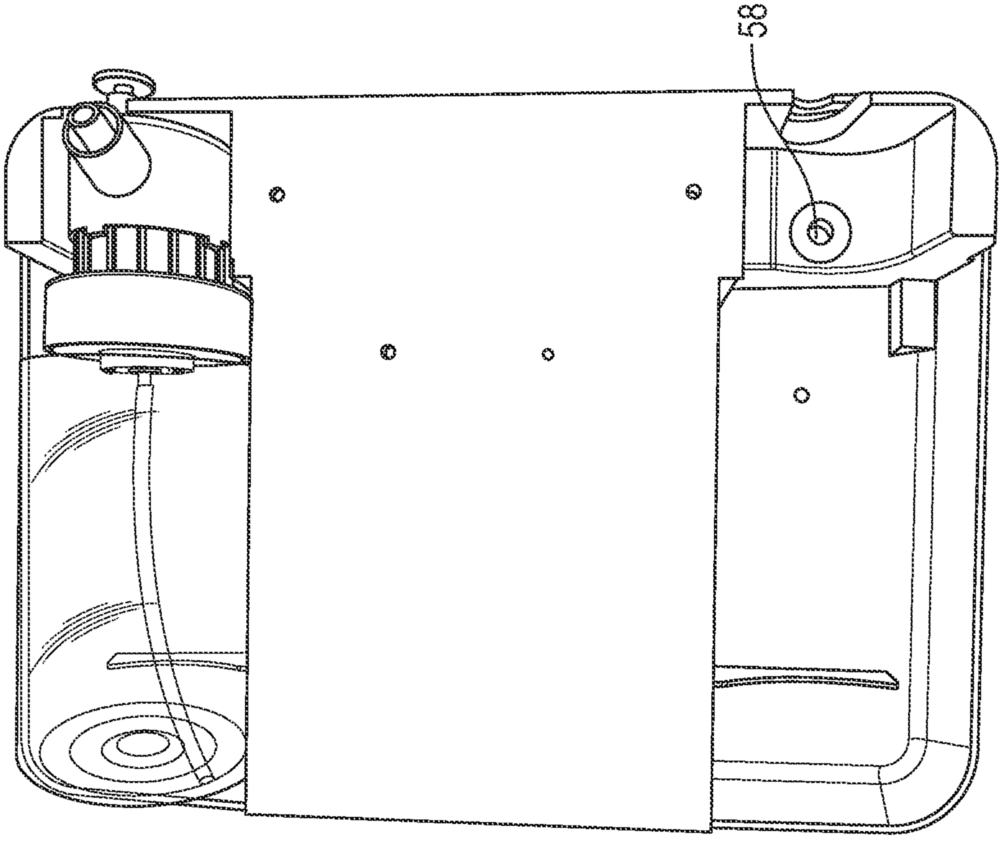
FIG. 14 is a top view of the rear panel of the scent dispenser of FIG. 10.

Like the dispenser implementation 2 previously described, magnetic fasteners 52 are used to hold the covers together, which may be any magnetic fastener type previously disclosed in this document. A right handed atomizer 54 and a left handed atomizer 56 are included in this dispenser implementation. The atomizers 54, 56 are the same structure and function in the same way as the atomizer 18 previously described other than the difference in the orientation of the various components. FIG. 14 illustrates how both atomizers are held in place through mounting openings 58 through which both atomizers/diffusers receive electrical power to operate.

In various implementations, the rear cover of both dispensers includes a power supply and one or more circuit boards that in combination form a control system designed to control the operation of the atomizer(s) included in each dispenser. In various implementations, the power supply may be a 12 V power supply. The one or more circuit boards may include a wireless module, like a module marketed under the tradename BLUETOOTH by Bluetooth SIG, Inc. of Kirkland, Washington. In other implementations, however, other wireless telecommunication protocols may be utilized, including, by non-limiting example, WiFI, Zigbee, 802.11, or any other wireless telecommunication system. The use of the Bluetooth module or other wireless module may allow for the custom programming of the dispensing times and frequencies of the atomizer(s) in each dispenser. Since the dispenser implementation 34 contains two different reservoirs, different scents can be included in each reservoir, allowing for, along with the appropriate programming, the creation of a wide variety of possible scent profiles and scent combinations using the different scents in the reservoirs. The ability to set timers on scent dispensing by the atomizers may also allow users to avoid dispensing too much scent or any scent during times when air handling systems and/or occupants are not present.

In the various dispenser implementations disclosed herein, the front cover/panel and rear cover/panel may be formed using a molding process, such as, by non-limiting example, injection molding, vacuum forming, casting, or any other molding process. In other implementations, the front cover/panel and rear cover/panel may be formed using three-dimensional printing. The various components of the diffusers/atomizers disclosed herein may be formed of metals, plastics, and semiconductor materials according to those described in the previously identified atomizer/diffuser references incorporated by reference herein. The electrical control system may include various components, including, by non-limiting example, metals, plastics, rubbers, insulators, semiconductor materials, battery components, circuit board materials, or any other electronics or power system component. The various plugs may be formed of any of a wide variety of materials, including, by non-limiting example, plastics, metals, metal alloys, ceramics, rubbers, or any other rigid or semi-rigid material capable of stopping flow through the dispensing orifices.

In places where the description above refers to particular implementations of scent dispensers and implementing components, sub-components, methods and sub-methods, it should be readily apparent that a number of modifications may be made without departing from the spirit thereof and that these implementations, implementing components, sub-components, methods and sub-methods may be applied to other scent dispensers.

What is claimed is:

1. A scent dispenser comprising:
- a front panel and a rear panel, the front panel having a side surface extending around edges of the front panel and the rear panel having a side surface extending around edges of the rear panel, the side surface of the front panel and the side surface of the rear panel configured to align to form an enclosure therein;
- a first dispensing opening in the front panel;
- a second dispensing opening formed partly in the side surface of the front panel and partly in the side surface of the rear panel;
- a diffuser supported in the enclosure, the diffuser comprising a first dispensing orifice extending toward the first dispensing opening and a second dispensing orifice extending toward the second dispensing opening; and
- a plug configured to be inserted into either the first dispensing orifice or the second dispensing orifice.

2. The scent dispenser of claim 1, wherein the front panel and the rear panel are coupled together through magnetic fasteners.

3. The scent dispenser of claim 1, wherein the rear panel comprises a mounting structure configured to mount the scent dispenser to a support surface.

4. The scent dispenser of claim 1, wherein an alignment of the first dispensing opening from the second dispensing opening is substantially 90 degrees.

5. The scent dispenser of claim 1, wherein the diffuser comprises a mounting projection configured to be received into a mounting port of the rear panel.

6. The scent dispenser of claim 5, wherein the mounting projection comprises an electrically conductive portion that electrically couples the diffuser with an electrical control system.

7. The scent dispenser of claim 1, wherein the rear panel comprises at least one air intake opening therein in fluid connection with an air intake of the diffuser.

8. A scent dispenser comprising:
- a front panel and a rear panel, the front panel having a side surface extending around edges of the front panel and the rear panel having a side surface extending around edges of the rear panel, the side surface of the front panel and the side surface of the rear panel configured to align to form an enclosure therein;
- a first dispensing opening and a third dispensing opening in the front panel;
- a second dispensing opening and a fourth dispensing opening formed partly in the side surface of the front panel and partly in the side surface of the rear panel;
- a first diffuser supported in the enclosure, the first diffuser comprising a first dispensing orifice extending toward the first dispensing opening and a second dispensing orifice extending toward the second dispensing opening;
- a second diffuser supported in the enclosure, the second diffuser comprising a third dispensing orifice extending toward the third dispensing opening and a fourth dispensing orifice extending toward the fourth dispensing opening;
- a first plug configured to be inserted into either the first dispensing orifice or the second dispensing orifice; and
- a second plug configured to be inserted into either the third dispensing orifice or the fourth dispensing orifice.

9. The scent dispenser of claim 8, wherein the front panel and the rear panel are coupled together through magnetic fasteners.

10. The scent dispenser of claim 8, wherein the rear panel comprises a mounting structure configured to mount the scent dispenser to a support surface.

11. The scent dispenser of claim 8, wherein an alignment of the first dispensing opening from the second dispensing opening is substantially 90 degrees and an alignment of the third dispensing opening from the fourth dispensing opening is substantially 90 degrees.

12. The scent dispenser of claim 8, wherein the first diffuser comprises a first mounting projection configured to be received into a first mounting port of the rear panel and the second diffuser comprises a second mounting projection configured to be received into a second mounting portion of the rear panel.

13. The scent dispenser of claim 12, wherein the first mounting projection and the second mounting projection each comprise an electrically conductive portion that electrically couples the first diffuser and the second diffuser, respectively, with an electrical control system.

14. The scent dispenser of claim 8, wherein the rear panel comprises at least one air intake opening therein in fluid connection with an air intake of the first diffuser and with an air intake of the second diffuser.

15. A scent dispenser comprising:
- a front cover and a rear cover surrounding an enclosure therein, the front cover and rear cover comprising a side surface between the front cover and the rear cover;
- a first dispensing opening in the front panel;
- a second dispensing opening formed in the side surface;
- a diffuser supported in the enclosure, the diffuser comprising a first dispensing orifice extending toward the first dispensing opening and a second dispensing orifice extending toward the second dispensing opening; and
- a plug configured to be inserted into either the first dispensing orifice or the second dispensing orifice.

16. The scent dispenser of claim 15, wherein the front cover and the rear cover are coupled together through magnetic fasteners.

17. The scent dispenser of claim 15, wherein an alignment of the first dispensing opening from the second dispensing opening is substantially 90 degrees.

18. The scent dispenser of claim 15, wherein the diffuser comprises a mounting projection configured to be received into a mounting port of the rear cover.

19. The scent dispenser of claim 18, wherein the mounting projection comprises an electrically conductive portion that electrically couples the diffuser with an electrical control system.

20. The scent dispenser of claim 15, wherein the rear cover comprises at least one air intake opening therein in fluid connection with an air intake of the diffuser.

* * * * *